United States Patent
Wellman, Jr. et al.

(10) Patent No.: US 9,415,366 B2
(45) Date of Patent: Aug. 16, 2016

(54) SYSTEMS AND METHODS FOR PROCESSING VARIABLE ACETYL STREAMS

(71) Applicant: Eastman Chemical Company, Kingsport, TN (US)

(72) Inventors: Gregory Abbott Wellman, Jr., Kingsport, TN (US); Joseph Nathaniel Bays, Kingsport, TN (US); Robert Sterling Kline, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 359 days.

(21) Appl. No.: 13/827,124

(22) Filed: Mar. 14, 2013

(65) Prior Publication Data

US 2014/0187812 A1    Jul. 3, 2014

Related U.S. Application Data

(60) Provisional application No. 61/747,567, filed on Dec. 31, 2012.

(51) Int. Cl.
| | |
|---|---|
| *C07C 51/087* | (2006.01) |
| *C07C 51/44* | (2006.01) |
| *B01J 19/00* | (2006.01) |
| *C07C 51/573* | (2006.01) |
| *C07C 67/00* | (2006.01) |

(52) U.S. Cl.
CPC ............... *B01J 19/00* (2013.01); *C07C 51/087* (2013.01); *C07C 51/44* (2013.01); *C07C 51/573* (2013.01); *C07C 67/00* (2013.01)

(58) Field of Classification Search
CPC ........ B01J 19/00; C07C 51/087; C07C 51/44; C07C 51/573
USPC .................. 562/517, 519, 890, 891; 560/231
See application file for complete search history.

(56) References Cited

U.S. PATENT DOCUMENTS

| 4,939,294 A | 7/1990 | Agreda |
| 7,737,298 B2 | 6/2010 | Kline et al. |
| 2012/0123156 A1 | 5/2012 | Wellman, Jr. et al. |

FOREIGN PATENT DOCUMENTS

| DE | 2423079 A1 * | 11/1975 | ............ C07C 51/087 |
| EP | 0 087 869 A1 | 9/1983 | |
| GB | EP 0087087 | * 2/1983 | |
| WO | WO 2012/064832 A1 | 5/2012 | |
| WO | WO 2012/074628 A1 | 6/2012 | |

OTHER PUBLICATIONS

Notification of Transmittal of the International Search Report and the Written Opinion of the International Searching Authority, or the Declaration date of mailing Mar. 20, 2014 received in International Application No. PCT/US2013/076658.

* cited by examiner

*Primary Examiner* — Kamal Saeed
*Assistant Examiner* — Janet L Coppins
(74) *Attorney, Agent, or Firm* — James Arnold, Jr.

(57) ABSTRACT

The invention provides systems and processes for concentrating acetic acid and acetic anhydride streams. The systems allow operation of equipment used for such concentrations in two or more modes of operation. At least one mode is intended to produce a concentrated or purified acetic acid stream. At least one other mode is intended to produce a concentrated or purified acetic anhydride stream.

49 Claims, No Drawings

SYSTEMS AND METHODS FOR PROCESSING VARIABLE ACETYL STREAMS

CROSS-REFERENCE TO RELATED APPLICATION

This application claims priority to U.S. Provisional Application Ser. No. 61/747,567 filed Dec. 31, 2012, the disclosure of which is incorporated herein by reference in its entirety except to the extent that it would conflict with the definition of terms herein.

BACKGROUND OF THE INVENTION

Many processes result in the formation of streams containing acetic acid and acetic anhydride. Carbonylation processes are an example. Carbonylation coproduction technologies exist in which both methanol and methyl acetate are carbonylated together to produce a product mixture of acetic acid and acetic anhydride. Some examples are described in European Patent Application having a Publication No. EP0087869. Some methyl acetate carbonylation processes use acetic acid as a solvent, so that the product stream contains both the acetic anhydride product and the acetic acid solvent. Furthermore, some acetic anhydride manufacturing processes include steps in which a portion of the acetic anhydride product is reacted with methanol to produce acetic acid (along with methyl acetate) such as described in U.S. Pat. No. 7,737,298 and U.S. Patent Application having Publication No. 2012/0123156. Such processes allow alteration of the relative amounts of acetic acid and acetic anhydride in the resulting stream. Streams may also be partially hydrolyzed with water to convert some of the acetic anhydride to acetic acid.

Acetic anhydride and acetic acid products are often separated and purified for sale or use in subsequent reactions. It may also be advantageous in some cases to combine acetic acid products containing small amounts of acetic anhydride with water to hydrolyze the acetic anhydride and thus produce an aqueous acetic acid solution. The separation and purification of two product streams results in capital and operating expense associated with two lines of equipment. It would be advantageous to identify ways to reduce such costs.

SUMMARY OF THE INVENTION

The invention provides systems and processes for concentrating acetic acid and acetic anhydride streams. The systems allow operation of equipment used for such concentrations in two or more modes of operation. At least one mode is intended to produce a concentrated or purified acetic acid stream. At least one other mode is intended to produce a concentrated or purified acetic anhydride stream. The invention thus affords the opportunity for costs savings by reducing the amount of separation equipment required. By allowing equipment to alternate between acetic acid and acetic anhydride mode, processes can be operated to produce only one type of product stream at a time, reducing or even eliminating the need for separate lines of equipment for concentration for streams for acid and anhydride products.

Thus, the invention provides systems for processing at least one acetyl feed composition, such acetyl feed composition containing acetic acid and acetic anhydride, wherein the system includes: (a) a first separation zone configured in a manner to separate a first separated stream from a first concentrated stream, and further configured such that the separation zone can be operated in an acid mode and can be operated in an anhydride mode; (b) at least one hydrolysis zone capable of operating a hydrolysis process to hydrolyze at least some acetic anhydride in the at least one acetyl feed composition to result in a hydrolyzed product stream containing acetic acid and water; (c) at least one feed conveyance component configured to allow transportation of at least some of the at least one acetyl feed composition to the first separation zone, the hydrolysis zone, or both; and (d) at least one hydrolyzed product conveyance component configured to allow transportation of at least some of the hydrolyzed product stream to the at least one first separation zone. The acid mode includes processing at least some of the hydrolyzed product stream in the first separation zone such that the first separated stream contains water and the first concentrated stream contains concentrated acetic acid, and the anhydride mode includes processing at least some of the acetyl feed composition in the first separation zone such that the first separated stream contains acetic acid and the first concentrated stream contains concentrated acetic anhydride. The at least one feed conveyance component and the hydrolysis process are configured such that: (a) while the first separation zone operates in the acid mode, the hydrolysis process can be operated in the hydrolysis zone and more than about 50% by weight of the acetyl feed composition can be fed to the hydrolysis zone; and (b) while the first separation zone operates in the anhydride mode at least about 50% by weight of the acetyl feed composition can be fed to the separation zone without undergoing a hydrolysis process.

In some embodiments, when the first separation zone operates in the anhydride mode, at least about 50% of the acetyl feed composition can travel through the hydrolysis zone without undergoing a hydrolysis process before being fed to the first separation zone. In some embodiments, when the first separation zone operates in the anhydride mode, at least about 50% of the acetyl feed composition can be fed to fed to the first separation zone without first being fed to the hydrolysis zone. In some embodiments, the system further includes at least one first separated stream recycling component capable of recycling at least some of the first separated stream to the hydrolysis zone. In some embodiments, the system further includes at least one first separated stream transfer component capable of transferring at least some of the first separated stream to at least one additional equipment or process (e.g., an esterification process. In some embodiments, the system further includes cooling components capable of removing heat from at least part of the hydrolysis zone, at least some of the feed to the hydrolysis zone, or both.

In some embodiments, the first separation zone includes a distillation column, the first separated stream is removed from at least one first location on the distillation column, the first concentrated stream is removed from at least one second location on the distillation column and the first location is vertically above the second location. Thus, for example first separated stream may include at least one distillation overhead or first sidedraw from the distillation column and the first concentrated stream may include at least one distillation underflow or second sidedraw from the distillation column. The first separated stream may include at least one distillation overhead from the distillation column and the first concentrated stream may include at least one distillation underflow from the distillation column. The first separated stream may include at least one distillation overhead from the distillation column, the first concentrated stream may include at least one sidedraw from the distillation column, and the system is capable of removing an underflow separated stream as a distillation underflow from the distillation column.

The system may further include at least one second separation zone configured to receive at least some of the first concentrated stream from the first separation zone and to separate at least one second separated stream from a second concentrated stream, and further configured to operate in either a second separation zone acid mode or a second separation zone anhydride mode. The second separation zone acid mode includes processing at least some of the first concentrated stream in the second separation zone such that the at least one second separated stream contains concentrated impurities and the second concentrated stream contains concentrated acetic acid, and the second separation zone anhydride mode includes processing at least some of the first concentrated stream in the second separation zone such that the at least one second separated stream contains concentrated impurities and the second concentrated stream contains concentrated acetic anhydride. The second separation zone may include a second distillation column such that the at least one second separated stream is removed from at least one first location on the second distillation column, the second concentrated stream is removed from at least one second location on the second distillation column and the at least one first location is vertically below the second location. Thus, the at least one second separated stream may include at least one distillation underflow or second sidedraw from the second distillation column and the second concentrated stream may include at least one distillation overhead or first sidedraw from the second distillation column. The at least one second separated stream may include at least one distillation underflow from the second distillation column and the second concentrated stream may include at least one distillation overhead from the second distillation column. The at least one second separated stream may include at least one distillation underflow from the second distillation column, the second concentrated stream may include at least one sidedraw from the second distillation column, and a third separated stream is removed as a distillation overhead from the second distillation column.

The system may further include at least one upstream production system capable of producing the acetyl feed composition, wherein the at least one upstream production system is configured to allow: (a) operation in an upstream process acid mode to produce an acid mode acetyl feed composition; and (b) operation in an upstream process anhydride mode to produce an anhydride mode acetyl feed composition, wherein the acid mode acetyl feed composition has an acid:anhydride ratio having an acid number that is at least about 10 higher than an acid number of the anhydride mode acetyl feed composition. In some examples of such embodiments, the acid mode acetyl feed composition has an acid:anhydride ratio having an acid number that is at least about 50 higher than an acid number of the anhydride mode acetyl feed composition.

The at least one upstream production system is configured to allow combining at least part of the at least one acetyl feed composition with at least some water, at least some methanol or both. The at least one upstream production system may include at least one carbonylation system capable of reacting carbonylation process feed compounds to produce a carbonylation product containing acetic acid, acetic anhydride or a combination thereof. In some embodiments, the system is configured to allow varying the weight ratio of methanol to total anhydride-forming reactants that form acetic anhydride in the carbonylation process feed compounds, wherein total anhydride-forming is the sum of amounts of methyl acetate and dimethyl ether in the carbonylation process feed compounds. In some embodiments the at least one upstream production system is configured to allow combining at least some of the carbonylation product with at least some water, at least some methanol or both.

The invention further provides methods that include operating one of the above systems in acid mode for a first period of time, operating such system in anhydride mode for a second period of time that is not concurrent with the first period of time. The invention further provides processes for processing a plurality of acetyl feed compositions containing acetic acid and acetic anhydride, which include: (a) operating a first separation process configured in a manner to separate compositions into a first separated stream and a first concentrated stream, and further configured to operate in either an acid mode or an anhydride mode; (b) while operating the first separation process in an acid mode, hydrolyzing at least one first acetyl feed composition in a hydrolysis process in a hydrolysis zone to produce a hydrolyzed product stream containing acetic acid and water, and feeding at least some of the hydrolyzed product stream to the first separation process; and (c) while operating the first separation process in an anhydride mode, bypassing at least one second acetyl feed composition around the hydrolysis process and feeding it to the first separation process. The acid mode includes operating the first separation process such that the first separated stream contains water and the first concentrated stream contains concentrated acetic acid, and anhydride mode includes operating the first separation process such that the first separated stream contains acetic acid and the first concentrated stream contains concentrated acetic anhydride.

In some embodiments of the above processes, the at least one first acetyl feed composition has an acid number in the acid:anhydride ratio that is no more than about 10 higher than the acid number in the acid:anhydride ratio of the second acetyl feed composition. In some embodiments, the at least one first acetyl feed composition has an acid number in the acid:anhydride ratio that is at least about 20 higher than the acid number in the acid:anhydride ratio of the second acetyl feed composition.

In some embodiments, bypassing at least one second acetyl feed composition around the hydrolysis process includes passing at least some of the at least one second acetyl feed composition through the hydrolysis zone without undergoing a hydrolysis process before being fed to the first separation zone. In some embodiments, bypassing at least one second acetyl feed composition around the hydrolysis process and feeding at least some of the at least one second acetyl feed composition to the first separation zone without first feeding it the hydrolysis zone.

In some embodiments, the process further includes recycling at least some of the first separated stream to the hydrolysis zone while the first separation process is operating in acid mode. In some embodiments, the process further includes transferring at least some of the first separated stream to at least one additional equipment or process (e.g. an esterification process). In some embodiments, the process further includes cooling at least part of the hydrolysis zone, at least some of the feed to the hydrolysis zone, or both.

In some embodiments, the first separation zone includes a distillation column, the first separated stream is removed from at least one first location on the distillation column, the first concentrated stream is removed from at least one second location on the distillation column, and the first location is vertically below the second location. For example, the first separated stream may include at least one distillation overhead or first sidedraw from the distillation column and the first concentrated stream may include at least one distillation underflow or second sidedraw from the distillation column.

The first separated stream may include at least one distillation overhead from the distillation column and the first concentrated stream may include at least one distillation underflow from the distillation column. The first separated stream may include at least one distillation overhead from the distillation column, the first concentrated stream may include at least one sidedraw from the distillation column, and an underflow separated stream may be removed as a distillation underflow from the distillation column.

The process may also include feeding at least some of the first concentrated stream to at least one second separation zone and withdrawing from the second separation zone a second separated stream from a second concentrated stream, wherein: the at least one second separation zone is configured to operate in either a second separation zone acid mode or a second separation zone anhydride mode; the at least one second separation zone acid mode includes processing at least some of the first concentrated stream in the at least one second separation zone such that the second separated stream contains concentrated impurities and the second concentrated stream contains concentrated acetic acid, and the at least one second separation zone anhydride mode includes processing at least some of the first concentrated stream in the second separation zone such that the second separated stream contains concentrated impurities and the second concentrated stream contains concentrated acetic anhydride. Such processes may further include operating the at least one second separation zone in second separation zone acid mode while operating the at least one first separation zone in acid mode, and operating the at least one second separation zone in anhydride mode while operating the at least one first separation zone in anhydride mode.

In some embodiments, the second separation zone may include a second distillation column, with the at least one second separated stream being removed from at least one first location on the second distillation column, the second concentrated stream being removed from at least one second location on the second distillation column and the first location being vertically below the second location. For example, the at least one second separated stream may include at least one distillation underflow or second sidedraw from the second distillation column and the second concentrated stream may include at least one distillation overhead or sidedraw from the second distillation column. The at least one second separated stream may include at least one distillation underflow from the second distillation column and the second concentrated stream may include at least one distillation overhead from the second distillation column. The at least one second separated stream contains at least one distillation underflow from the second distillation column, the second concentrated stream may include at least one sidedraw from the second distillation column, and a third separated stream may be removed as a distillation overhead from the second distillation column.

The processes may further include operating at least one upstream process in an upstream process acid mode to produce an acid mode acetyl feed composition and operating the at least one upstream process in an upstream process anhydride mode to produce an anhydride mode acetyl feed composition, wherein: the acid mode acetyl feed composition has an acid:anhydride ratio having an acid number that is at least about 10 higher than an acid number of the anhydride mode acetyl feed composition; at least one first acetyl feed composition is an acid mode acetyl feed composition; and at least one second acetyl feed composition is an anhydride mode acetyl feed composition. In some embodiments, the acid mode acetyl feed composition has an acid:anhydride ratio having an acid number that is at least about 50 higher than an acid number of the anhydride mode acetyl feed composition. In some embodiments, the upstream process acid mode includes combining at least one acetyl feed composition with at least some water, at least some methanol or both.

In some embodiments, the at least one upstream process includes at least one carbonylation process that includes reacting carbonylation process feed compounds to produce a carbonylation product containing acetic acid and acetic anhydride. The carbonylation process may include carbonylating methanol and at least one anhydride-forming reactant, wherein: the at least one anhydride-forming reactant is selected from acetic anhydride, dimethyl ether, or a combination thereof; upstream process acid mode includes feeding the carbonylation process in a weight ratio of methanol to total reactants that form acetic anhydride that is higher than the weight ratio of methanol to total reactants that form acetic anhydride in upstream process anhydride mode; and total reactants that form acetic anhydride is the sum of amounts of acetic anhydride and dimethyl ether in the carbonylation process feed compounds.

DETAILED DESCRIPTION

The invention provides systems and processes useful in preparing concentrated acetic acid and concentrated acetic anhydride streams from acetyl feed compositions. The systems and processes allow operation of equipment in either an acid mode or an anhydride mode. As such, the systems and processes can result in product streams having concentrated acetic acid or having concentrated acetic anhydride.

Systems and Processes

In some embodiments, the present invention provides flexible systems and processes that may operate in either acid mode or anhydride mode. The systems include at least one hydrolysis zone or process and at least one separation zone or process that can be used to concentrate acetic acid or acetic anhydride. The system further includes conveyance components to transport compositions into and between components of the system. In some embodiments, processes of the invention include operating the systems of the invention in an acid mode for a first period of time and operating the systems in an anhydride mode for a second period of time that is not concurrent with the first period of time. In some embodiments, the processes of the invention include operating a first separation zone or separation process configured in a manner to separate compositions into a first separated stream and a first concentrated stream, and further configured such that the separation zone or process can be operated in an acid mode and can be operated in an anhydride mode. The invention provides systems and processes that include operating that first separation process in an acid mode while hydrolyzing at least one acetyl feed composition in a hydrolysis process in a hydrolysis zone or process to produce a hydrolyzed product stream that contains acetic acid and water and feeding at least some of the hydrolyzed product stream to the first separation process. Such processes and systems further include operating the first separation process in an anhydride mode, while bypassing at least some of the acetyl feed composition around the hydrolysis process and feeding it to the first separation process without hydrolysis.

The systems and processes are configured such that the at least one separation zone or process can be operated in an acid mode and can be operated in anhydride mode. This allows the same equipment to be used for two modes of purification operations that can allow campaigning of production between acetic acid streams and acetic anhydride streams.

Acid Mode and Anhydride Mode

As used throughout this application, "anhydride mode" shall refer to operating in a configuration and under such parameters as to result in a product stream containing concentrated acetic anhydride. As used throughout this application, "acid mode" shall refer to operating in a configuration and under such parameters as to result in a product stream containing concentrated acetic acid. As used throughout this application, "concentrating" a material such as acetic acid or acetic anhydride (or producing a stream in which such material is "concentrated) in a stream resulting from a process, system or part thereof shall mean production of a stream in which the concentration of such material is higher than the concentration of that material in the streams or compositions fed to the process, system or part thereof or has a lower concentration of impurities than was contained in the streams or compositions fed. Thus, in some embodiments in which such impurities are present in very small amounts, the measured concentration of the "concentrated" material may not appear to increase, but the measured concentration of the impurities may decrease. Similarly, "concentrating" an impurity into a stream resulting from a process, system or part thereof shall mean production of a stream in which the concentration of such impurity is higher than the concentration of that impurity in the streams or compositions fed to the process.

While several components of the systems and processes of the invention may be adjusted in acid and anhydride mode, the first separation zone or process of the invention are particularly influenced by switching between acid and anhydride mode. In acid mode, the first separation zone or process operates to separate a separated stream containing water from a concentrated stream containing concentrated acetic acid. In anhydride mode, the first separation zone or process operates to separate a separated stream containing acetic acid from a concentrated stream containing concentrated acetic anhydride.

In some embodiments of acid mode, more than about 50% by weight of the acetyl feed composition can be fed to at least one hydrolysis zone or process before being fed to the separation zone or process. A hydrolysis process occurs in the at least one hydrolysis zone. In some embodiments, greater than about 99.5% of the acetyl stream is fed to at least one hydrolysis zone. Embodiments also exist in which the portion (by weight) of the acetyl feed composition fed to the at least one hydrolysis zone or process is at least about 60%, at least about 70%, at least about 80%, at least about 90%, at least about 95%, at least about 97.5%, or at least about 99%. As used throughout this application, all percentages are determined by weight unless specified otherwise.

In some embodiments of anhydride mode, at least about 50% by weight of the acetyl feed composition is fed to at least one separation zone or process after bypassing the at least one hydrolysis process. In some embodiments, greater than about 99.5% of the acetyl stream bypasses the at least one hydrolysis process. Embodiments also exist in which the portion (by weight) of the acetyl feed composition that bypasses the at least one hydrolysis process is at least about 60%, at least about 70%, at least about 80%, at least about 90%, at least about 95%, at least about 97.5%, or at least about 99%. In some embodiments, at least some of acetyl stream bypasses the at least one hydrolysis process by bypassing the hydrolysis zone. In some embodiments, at least some of acetyl stream bypasses the at least one hydrolysis process by passing through the at least one hydrolysis zone while hydrolysis is not occurring or is occurring at a diminished rate. The latter can be accomplished, for example, by limiting or eliminating water fed to or present in the at least one hydrolysis zone.

At least some of the acetyl stream that bypasses the at least one hydrolysis process is fed to at least one separation zone or process without undergoing the hydrolysis process. Embodiments exist in which at least about 50%, at least about 75%, at least about 90%, at least about 95%, at least about 98% or at least about 99% of the acetyl stream that bypasses the at least one hydrolysis process is fed to at least one separation zone or process. Some or all of the acetyl stream that bypass the at least one hydrolysis process may be fed to other vessels, zones or processes prior to being fed to the separation zone or process, but are not hydrolyzed.

Acetyl Feed Composition

The acetyl feed compositions used in the present invention contain acetic acid, acetic anhydride or both. The acetyl feed compositions contain more than 0% but less than 100% of acetic acid/anhydride. In some embodiments, the acetyl feed compositions contain more than 0% but less than 100% of acetic both acetic acid and acetic anhydride. As used throughout this application, the term "acetic acid/anhydride" or "acid/anhydride" in reference to a composition or a component of a composition shall be used generically to describe a composition or a component of a composition that is acetic acid, acetic anhydride, or a combination of the two. The stream may contain other components as impurities, depending on the original source of the stream and any subsequent processing of acetic acid/anhydride in the stream. For example, various embodiments exist in which the stream is at least about 80%, at least about 85%, at least about 90%, at least about 92.5%, at least about 95%, at least about 97.5%, at least about 99%, at least about 99.5%, or at least about 99.9% acetic acid/anhydride. Some examples of impurities that may be present include acetone, iodine-containing compounds (i.e. compounds present in a crude acetyl mixture that include at least one iodine atom or ion) methyl acetate, carboxylic acids and anhydrides other than acetic acid or acetic anhydride, ethylidene diacetate, tar and impurities from the source process. In some embodiments, the total amount of components other than the acetic acid/anhydride are no greater than about 0.1%. In some embodiments, the total amount of components other than the acetic acid and acetic anhydride are less than 1%.

The ratio of acetic acid to acetic anhydride in the acetyl feed compositions may be selected from a wide variety of values and ranges and may conveniently be referred to as an acid:anhydride ratio using a ratio is expressed such that the sum of the first and second number in the ratio equals 100. All ratios of acid to anhydride are presented such that the first numbers refer to acid content and that both numbers refer to amounts by weight. Embodiments exist for streams anywhere from about 0.5:99.5 to about 99.5 to 0.5. Some examples of ranges include from about 10:90 to about 90:10, from about 20:80 to about 80:20, from about 30:70 to about 50:50, from about 40:60 to about 60:40, from about 50:50 to about 70:30, from about 50:50 to about 95:5, from about 70:30 to about 95:5, from about 40:60 to about 20:80, from about 60:40 to about 80:20, from about 30:70 to about 10:90, from about 70:30 to about 90:10, from about 20:80 to about 1:99, from about 80:20 to about 99:1, from about 20:80 to about 10:90, from about 70:30 to about 90:10, from about 70:30 to about 85:15, from about 80:20 to about 90:10, from about 85:15 to about 95:5, from about 50:50 to about 99.9:0.1, from about 75:25 to about 99.9:0.1, from about 90:10 to about 99.9:0.1, and so on. As used throughout this application, the "acid number in the acid:anhydride ratio" refers to the first number in the acid:anhydride ratio.

The invention includes embodiments in which acetyl feed compositions having any the above compositions may be used while the system and process is operating in either anhydride mode or acid mode. Generally speaking, anhydride mode can be more cost efficient when the ratio of acid:anhydride in the acetyl feed composition is less than 50:50 and acid mode can be more cost efficient when the ratio of acid:anhydride is greater than 50:50 since these pairings take advantage of which components are present in greater amounts.

However, either mode may be used at any ratio. In some embodiments of anhydride mode, the ratio is from about 95:5 to about 0.5:99.5. In some embodiments of anhydride mode, the ratio is from about 50:50 to about 0.5:99.5. Embodiments of anhydride mode also exist in which the ratio is each of the following ranges: from about 25:75 to about 0.5:99.5, from about 40:60 to about 20:80, from about 30:70 to about 50:50, from about 35:65 to about 25:75, from about 30:70 to about 10:90, from about 45:55 to about 35:65, from about 15:85 to about 0.5:99.5, from about 10:90 to about 0.5:99.5 or from about 25:75 to about 15:85.

In some embodiments of acid mode, the ratio of acid:anhydride in the acetyl feed composition is from about 50:50 to about 99.5:0.5. Embodiments of acid mode also exist in which the ratio is each of the following ranges: from about 75:25 to about 99.5:0.5, from about 60:40 to about 80:20, from about 70:30 to about 50:50, from about 65:35 to about 75:25, from about 70:30 to about 90:10, from about 55:45 to about 65:35, from about 85:15 to about 99.5:0.5, from about 90:10 to about 99.5:0.5 or from about 75:25 to about 85:15.

Although acetic acid and acetic anhydride mode may each be used with any acid:anhydride ratio, it may be advantageous, based on operating and economic conditions, to use acid mode when the ratio is higher and to use anhydride mode when the ratio is lower. In some embodiments, the acid number in the acid:anhydride ratio for the acetyl feed composition while operating in acid mode is at least about 10 higher the acid number in the acid:anhydride ratio while operating in anhydride mode. In various embodiments, this number in acid mode is at least about 20, at least about 30, at least about 40, at least about 50 or at least than about 60 higher than in anhydride mode. The difference in the acid number may also be expressed as a range, such as from about 10 to about 50 higher than anhydride mode, from about 25 to about 75 higher, from about 25 to about 50 higher, from about 50 to about 99 higher, from about 50 to about 75 higher, from about 75 to about 99 higher, and so on. In some embodiments, the difference in the acid number may be expressed as being not greater than a certain number such as, no more than about 1 higher than anhydride mode, no more than about 2.5, no more than about 5 no more than about 10, no more than about 15 higher, no more than about 20 higher, and so on.

In some embodiments, the acetyls feed stream is derived from a carbonylation process or system. Although the invention is useful with acetyl feed compositions derived from carbonylation processes, it may be used with acetyls feed stream that originate or are derived from any source. As used throughout this application, "derived from" a carbonylation or other process means that the stream either originates from such process or was prepared from other intermediate processes that used or processed one or more streams that originated from such processes.

Streams from any carbonylation process may be used. Some examples include coproduction processes in which both acetic acid and acetic anhydride are formed by carbonylation and processes in which acetic anhydride is formed in the presence of acetic acid (for example, processes in which acetic acid is used as a solvent). In some embodiments, the carbonylation process includes continuously combining in at least one carbonylation reactor components that include carbon monoxide and at least one feedstock compound selected from methyl acetate, dimethyl ether or a combination of the two, to produce a first liquid reaction composition. The reactants are combined in the presence of a carbonylation catalyst metal (for example, rhodium, iridium or nickel), methyl iodide, and acetic acid under conditions effective to convert at least some of the feedstock compound to acetic anhydride. In some embodiments, the catalyst metal is rhodium. Other components, such as lithium compounds useful as promoters, may also be present. In some embodiments, one or more carbonylation reactors is operated at a temperature of from about 100 to about 300° C. and a pressure (total) of from about 21.7 to about 276.7 bars absolute (bara) and the residence time within each carbonylation reactors is from about 4 minutes to about 120 minutes. In some embodiments, one or more carbonylation reactors is operated at a temperature of from about 175 to 220° C. and a pressure (total) of about from 35.5 to about 104.4 bara, the residence time within the carbonylation reactors is from about 15 to about 40 minutes. The reaction results in the formation of a first liquid reaction composition that includes at least some unreacted feedstock compound, dissolved carbon monoxide and acetic anhydride product, along with acetic acid and other components that result from the catalyst cycle (for example, rhodium, lithium, and iodine-containing salts compounds or both). In some embodiments, the streams travel through two or more reactors configured in series. In embodiments involving additional reactors, additional reactants and other materials may be added in one or more of the downstream reactors. In some embodiments, additional carbon monoxide is fed to one or more of the downstream reactors.

In some embodiments, methanol as well as at least one additional feedstock compound selected from anhydride-forming reactants (i.e. methyl acetate, dimethyl ether or combinations of the two) are combined with carbon monoxide in the presence of a carbonylation catalyst metal (for example, Group VII metals, methyl iodide, under conditions effective to convert at least some of the methanol to acetic acid and at least some of the additional feedstock compound to acetic anhydride. In some embodiments, the catalyst metal is rhodium. Other components, such as compounds useful as promoters, may also be present. This reaction likewise results in the formation of a first liquid reaction composition that includes at least some unreacted feedstock compounds, dissolved carbon monoxide and acetic acid product as well as acetic anhydride product, along with other components that result from the catalyst cycle. In some embodiments, the streams travel through two or more reactors configured in series. In embodiments involving additional reactors, additional reactants and other materials may be added in one or more of the downstream reactors. In some embodiments, additional carbon monoxide is fed to one or more of the downstream reactors.

Some intermediate processes that may be used to process streams from carbonylation processes may include, for example, purification or concentration processes prior to feeding to the hydrolysis process or zone or first separation process or zone. Some examples include evaporation and flash processes used to separate process streams from higher boiling impurities, and separation processes to remove materials for recycle either higher boiling impurities, lower boiling impurities, or both. In some embodiments, removed components (for example, catalyst or promoter components) are recycled to upstream processes for use or reuse.

Variable Feed Streams and Upstream Process Acid and Anhydride Modes

In some embodiments, the one or more acetyl feed compositions are derived from one or more upstream processes or upstream systems capable of producing such compositions, and also capable of altering the ratio of acetic acid to acetic anhydride in the resulting acetyl feed compositions. For example, where acetyl feed compositions contain both acetic acid and acetic anhydride, upstream processes or systems may include or provide the capability to combine at least part of the acetyl feed compositions with at least some water, at least some methanol or both.

In some embodiments, the upstream processes or systems include carbonylation processes or systems that carbonylate methyl acetate, dimethyl ether, methanol or combinations of two or more of the foregoing to produce a carbonylation product. The carbonylation product may contain acetic acid, acetic anhydride or both. In some embodiments of carbonylation processes and systems in which both methanol and at least one additional anhydride-forming reactant (i.e. methyl acetate, dimethyl ether or both) are fed to a carbonylation process or system, the relative amounts of methanol and the anhydride-forming reactant can be manipulated. ethanol, water or both may be added to the carbonylation process or system to result in the formation of acetic acid. In some embodiments involving carbonylation reactors configured in series, methanol, water or both may be added in piping, vessels, or other containment through which a product composition leaves one carbonylation reactor and flows prior to introduction into a subsequent carbonylation reactor.

In some embodiments, acetyl feed compositions derived from a carbonylation process or system are processed after carbonylation in intermediate processes or systems that are capable of altering the ratio of acetic acid to acetic anhydride in the product stream, prior to introduction to the hydrolysis process or zone, first separation process or zone, or both. Some examples include processes that involve combining a carbonylation product stream with methanol, water or both. Such combination may occur in any suitable intermediate equipment or location. Some examples include piping, heat exchangers, equipment associated with separation processes such as flash, distillation or evaporation processes, and combinations of any of the foregoing.

Another way in which the composition of acetyl feed compositions can be manipulated is simply by blending an acetyl feed composition with one or more additional streams containing acetic acid, acetic anhydride or both in desired amounts. Yet another way is by changing one or more of the sources of the acetyl feed composition. For example, in some embodiments, the process or system of the invention may be used to process acetyl feed compositions from different processes or systems, and one or more sources of the acetyl feed compositions may be switched in whole or in part from one process or systems (or group of processes or systems) to one or more other such systems. In some embodiments, the acetyl feed composition may originate from a number of sources and streams from some sources may be added to or subtracted from the acetyl feed composition.

As can be seen, in many upstream processes and systems, it is possible to manipulate the acetyl feed composition in a number of ways to alter the ratio of acid:anhydride in the stream at one or more process locations upstream of the introduction of the acetyl feed composition into the hydrolysis process or zone or first separation process or zone of the present invention. Thus, in some embodiments, upstream production systems or processes can be seen as operating in an upstream process acid mode and an upstream process anhydride mode. As used throughout this application, upstream processes and upstream process systems that have an "upstream process acid mode" and an "upstream process anhydride mode" shall refer to upstream processes that are capable of varying the acid number in the acid:anhydride ratio of the acetyl feed composition by at least about 10. Thus, the acetyl feed composition produced by the upstream process acid mode has an acid:anhydride ratio has an acid number that is at least about 10 higher than the acid number of the acetyl feed composition produced by the upstream process anhydride mode. In some embodiments, these compositions are referred to as the "acid mode acetyl feed composition" and the "anhydride mode acetyl feed composition," respectively.

In various embodiments, the upstream processes may be capable of varying the acid number by at least about 15, at least about 20, at least about 25, at least about 30, at least about 35, at least about 40, at least about 45, at least about 50, at least about 55, at least about 60, at least about 65, at least about 70, at least about 80, at least about 90 and so on. The amount of variation may also be expressed as ranges, such as from about 10 to about 99, with 99 referring to a variation between streams that are 99.5:0.5 and 0.5:99.5. Some examples of additional ranges include from about 15 to about 99, from about 20 to about 99, from about 25 to about 99, from about 30 to about 99, from about 35 to about 99, from about 40 to about 99, from about 45 to about 99, from about 50 to about 99, from about 55 to about 99, from about 60 to about 99, from about 65 to about 99, from about 70 to about 99, from about 80 to about 99, from about 90 to about 99, from about 20 to about 80, from about 30 to about 70, from about 40 to about 60, from about 20 to about 50, from about 50 to about 80, from about 30 to about 60, from about 40 to about 70, and so on. As noted above, these numbers refer to the amount by which the acid number in the ratio in the composition produced by upstream process acid mode is higher than the acid number in the ratio in the composition produced by upstream process anhydride mode in various embodiments.

Thus, in some embodiments, the processes of the invention include operating at least one upstream process in both an upstream process acid mode to produce an acid mode acetyl feed composition and an upstream process anhydride mode to produce an anhydride mode acetyl feed composition and the systems of the invention are capable of operating in this manner. In some embodiments, the acid mode acetyl feed composition is the acetyl feed composition that is used while operating the separation process in acid mode and the anhydride mode acetyl feed composition is the acetyl feed composition that is used while operating the separation process in anhydride mode.

Hydrolysis Zone and Hydrolysis Process

Whenever acetyl feed compositions or portions thereof undergo a hydrolysis process, this is accomplished by contacting acetyl feed compositions (or portions thereof) with a stoichiometric excess of water and optionally an added hydrolysis catalyst. The water source is not critical and any suitable feed stream that contains a stoichiometric excess of water may be used. The invention is not limited to embodiments in which a single stream containing water is fed to the hydrolysis zone. In some embodiments, multiple sources of water are fed to the hydrolysis zone.

As used throughout this application, "stoichiometric excess of water" means more moles of water than the number of moles of acetic anhydride contained in the acetyl feed composition that is fed to hydrolysis reactor. In the hydrolysis process, a single molecule of water reacts with a given molecule of acetic anhydride to provide two molecules of acetic acid. More moles of water than acetic anhydride provides a stoichiometric excess. Thus, in a batch process, a greater number of moles of water are combined in the batch than the number of moles of acetic anhydride. In a continuous process, a greater number of moles of water per unit of time are fed to the hydrolysis zone than the number of moles of acetic anhydride fed during the same period.

The ratio of water to anhydride added to the hydrolysis process is not limiting, and may be tightened or relaxed based on the amount of water in the resulting hydrolyzed product stream that is considered acceptable. In some embodiments, the ratio of water to anhydride fed to the hydrolysis process is from about 1.05:1 to about 10:1. In some embodiments, the ratio of water to anhydride fed to the hydrolysis process is from about 3:1 to about 10:1. In some embodiments, ratio of water to anhydride fed to the hydrolysis process is from about 1.05:1 to about 1.4:1 (i.e. 5% to 40% molar excess of water). In some embodiments, the ratio of water to anhydride fed to the hydrolysis process is from about 1.05:1 to about 1.1:1. The stoichiometric ratio of water to acetic anhydride is selected as a value or range that is sufficiently low to allow downstream water-acid separation processes (e.g. distillation) to concentrate the acetic acid stream to a desired degree. In some embodiments involving use of an added hydrolysis catalyst, the degree of stoichiometric excess of water fed to the hydrolysis zone may be increased over time compensate for hydrolysis catalyst becoming spent or otherwise experiencing diminished efficacy with age or continued use.

Where used, the added hydrolysis catalyst may include one or more of any effective and otherwise suitable hydrolysis catalysts. Some criteria that may be considered in the selection of an appropriate catalyst are: the ability to catalyze the hydrolysis so as to cause it to occur at an acceptable rate; stability under the temperature and pressure used in the process; stability in the presence of the components of the stream being treated; and lifetime in process.

Where used, added hydrolysis catalysts may be present as liquids, solids, or both. Some examples of liquid catalysts include acids and bases such as sulfuric acid, phosphoric acid, hydrochloric acid, perchloric acid, sulfonic acids, pyridines (and various derivatives thereof), and cyclic or acyclic amines. In some embodiments, solid catalytic materials used as added hydrolysis catalysts incorporate one or more chemical functionalities of these liquid catalysts. Some examples of solid materials that may be used as added hydrolysis catalysts include resins, gels, zeolites, clays, aluminas, and silicas. Many of these materials can be modified either in physical form (e.g., structure, pore size, surface area, etc) or chemically (by addition of adsorbents, performing chemical exchange or chemical surface modifications, or moderation of either acidic or basic groups by any of these or other techniques). In some embodiments, the added hydrolysis catalyst is selected from a resin material. Some examples of such materials include certain AMBERLYST resins available from Rohm & Haas, Philadelphia, Pa., DOWEX 50 and DOWEX G26, available from Dow Chemical Company, Midland Mich. and PUROLITE C100H available from The Purolite Company, Bala Cynwyd, Pa. In some embodiments, the cation exchange material is a macroreticular polymeric cation exchange resin having the hydrogen form of a sulfonic acid. Examples of such resins include resins containing styrene divinylbenzene copolymers functionalized with sulfonic acid groups such as certain AMBERLYST resins, in particular AMBERLYST 15.

The amount of added hydrolysis catalyst used is not critical to the invention and any effective and desired amount may be added. Where used, the amount of added hydrolysis catalyst present within the hydrolysis zone will depend principally on the added hydrolysis catalyst employed, the flow rate and composition of the hydrolysis feed stream, the desired residence time in the catalyst area, and desired composition of the hydrolysis product stream. Where added hydrolysis catalyst resides in the hydrolysis zone for an extended period (e.g. a bed of solid catalyst used in a continuous process) an excess of catalyst may be charged to the bed initially to provide for continued effective catalysis as part of the added hydrolysis catalyst becomes spent or is otherwise experiences diminished efficacy with age or continued use.

Embodiments also exist in which the hydrolysis occurs without an added hydrolysis catalyst. In some embodiments, the decision about whether or not to use an added catalyst may depend upon what constitutes an acceptable rate of hydrolysis for the defined process. Carboxylic acids such as acetic acid or propionic acid present in the stream and produced in situ by the hydrolysis reaction is an example of an organic weak acid that may provide some catalysis in the absence of an added catalyst. Additionally, the use of elevated temperatures, pressures, or extended residence times may obviate the need to use an added catalyst to increase the rate of the hydrolysis reaction. Because of the weak catalysis performed by such carboxylic acid, the term "added hydrolysis catalyst" refers to a catalyst other than the carboxylic acid already present in the feed stream that is added to or otherwise contacted with the stream in the hydrolysis zone.

In some embodiments, the hydrolysis zone may include a first sub-zone that does not contain added hydrolysis catalyst and a second sub-zone that contains added hydrolysis catalyst. The configuration can be helpful, for example, in embodiments in which the feed to the hydrolysis process is rich in the anhydride because higher concentrations of anhydride have less need for added hydrolysis catalyst. In some embodiments, an initial hydrolysis sub-zone without added hydrolysis catalyst is used to reduce the anhydride concentration of a rich stream, and a second hydrolysis sub-zone with added hydrolysis catalyst is then used to further treat the lower concentrations of anhydride.

The location and configuration of the hydrolysis zone is not critical. The zone may be any type of location or containment that can be configured to catalyze the reaction, and if desired, remove desired amounts of heat generated by the hydrolysis reaction. Some examples include vessels, tanks, pipes and combinations of any of the foregoing. The size and configuration depends on the amount of acetic anhydride to be hydrolyzed. Where solid added hydrolysis catalyst is used, some examples of hydrolysis zone configurations include packed beds, packed pipes, and other equipment which can be used to cause contact of one or more liquid feed streams with the added hydrolysis catalyst. In some embodiments, the hydrolysis zone is a catalyst-packed bed. In some embodiments, the hydrolysis zone receives a mixed stream containing the hydrolysis feed stream and the water feed stream. The mixture enters the hydrolysis zone from the top, is distributed by a liquid distribution device, and flows in a downflow mode, flowing over the added hydrolysis catalyst and exiting the bottom of the hydrolysis zone. The hydrolysis feed stream, water feed stream, and any other streams may be fed to a vessel as separate streams or as part of a mixture that is first combined prior to introduction into the vessel. The hydrolysis zone may or may not include liquid distribution devices such as shower heads, spray nozzles, or liquid distribution trays. If fed separately, the hydrolysis feed stream and water feed stream may be fed in any suitable fashion. The stream or streams fed to the hydrolysis zone may flow in an upflow or downflow mode. Any effective material of construction may be used for the hydrolysis zone. In some embodiments, the hydrolysis zone is sufficiently corrosion-resistant for the range of compositions between the hydrolysis feed and the hydrolysis product. For example, in some embodiments, all or part of the hydrolysis zone is constructed of a high-nickel alloy such as Alloy C-276. In some embodiments, all or part of the hydrolysis zone is constructed of lower performance alloy such as 300 series stainless steels.

The design of the hydrolysis zone, including selection and sizing of equipment and selection and quantity of added hydrolysis catalyst can be readily determined based on literature data, standard engineering calculations, or mathematical models. The composition, volume and temperature of the hydrolysis feed stream should be considered. In some embodiments, a hydrolysis zone design is based on the scale up of a pilot reactor described by a residence time of at least about 7.4 minutes and a superficial velocity of about 0.45 meters per minute.

The hydrolysis zone results in a hydrolyzed product stream, in which at least some of the acetic anhydride molecules have been hydrolyzed to the corresponding acetic acid. In some embodiments, the anhydride content is less than 1%. In some embodiments, the anhydride content is less than 0.5%. In some embodiments, the anhydride content is less than 0.1%. In some embodiments, the anhydride content is below detectable limits. In some embodiments, the anhydride content is zero. The hydrolyzed product stream also contains water due to the stoichiometric excess.

Optional Cooling

In some embodiments, the process further contains at least one cooling process or step. The cooling process cools one or more feeds to the hydrolysis zone, or the material within the hydrolysis zone. The cooling process can help to counteract the exotherm from the hydrolysis process, especially when higher concentrations of anhydride are included in the overall feed. This can be particularly beneficial, for example, when dealing with added hydrolysis catalysts that can degrade at elevated temperatures, but may be used in any configuration where cooling is desired.

Cooling takes place in a cooling zone, which may be include some or all of a hydrolysis zone, areas separate from a hydrolysis zone, or both. The location and configuration of the optional cooling zone is not critical and any desirable type of location or containment that can be configured to remove a heat can be used. Some examples include one or more shell-and-tube heat exchangers, one or more plate-and-frame heat exchangers, one or more double-pipe exchangers, or other equipment which transfers heat from the warm hydrolysis reaction mixture to a cool utility or process stream such as water, air, or other fluids. In some embodiments, the cooling zone may include a shell-and-tube heat exchanger. Some or all of the heat exchanging equipment in a cooling process may be deactivated in certain process scenarios, thus allowing the hydrolysis unit to process a variety of concentrations of acetic anhydride but allowing reduction or elimination of heat exchange operation when necessary. Cooling medium may be water or any other suitable coolant.

In some embodiments, one or more cooling process is combined with a hydrolysis zone, for example, by using a heat exchanger packed with solid hydrolysis catalyst. In some embodiments, the cooling process occurs in one or more separate cooling zones. Combinations may also be used, such as embodiments having a cooled hydrolysis zone and a cooling zone upstream of the hydrolysis zone. Any effective or desirable configurations of cooling processes and hydrolysis zones may be used. Some examples include arrangement of cooling zones in series or parallel upstream from the hydrolysis zone, one or more cooling zones followed by one or more hydrolysis zones arranged in series or parallel with the one or more cooling zones. In some embodiments, the process includes one shell-and-tube heat exchanger acting as a cooling zone and arranged in series directly upstream from one packed bed acting as a hydrolysis zone. The cooling process may also be configured to cool only one of the feeds to the hydrolysis zone, or a combination of feeds.

Separation Zone and Separation Process

At least one separation zone or separation process is used to concentrate desired products from hydrolyzed product streams that result from the hydrolysis process as well as acetyl feed composition that bypass the hydrolysis process (for example, by bypassing the hydrolysis zone or by passing through the hydrolysis zone without undergoing hydrolysis). When operating in acid mode, at least some of the hydrolyzed product stream is fed to the separation zone or process to separate water from the hydrolyzed product stream and to concentrate the acetic acid. When operating in anhydride mode, at least some of the acetyl feed composition that bypasses the hydrolysis process is fed to the separation zone or process to separate acid from the hydrolyzed product stream and to concentrate the acetic anhydride.

Any effective separation zone or process may be used, including, for example, distillation vessels such as distillation columns. In some embodiments, the separation process is a distillation process or system, such as a distillation column and related equipment allowing use for separation. In some embodiments, a concentrated stream having the desired level of purity is taken from the distillation column at a location that is vertically below the location at which the separated stream is taken from the column. For example, in some embodiments, the concentrated stream is taken from the underflow of the distillation process and the separated stream is taken from the overhead or a sidedraw. In some embodiments, the concentrated stream is taken from a sidedraw and the separated stream is taken from the overhead or a second sidedraw that is vertically above the first sidedraw. In some embodiments, the concentrated stream is taken as an underflow and the separated stream is taken as a sidedraw. In some embodiments, the at least one separated stream is a distillation overhead from the distillation column, and the concentrated stream is at least one sidedraw from the first distillation column, while another separated underflow stream is removed as an underflow. This configuration may be used, for example, to separate higher boiling impurities from the stream. The equipment and parameters of the separation zone or process are not critical as any effective process or equipment for separating the streams in each mode may be used. The equipment is sized and constructed in a manner that will accommodate the difference in parameters between acid mode and anhydride mode. For example, temperatures, pressures and reflux ratios when separating acetic acid and concentrating an acetic anhydride stream differ from those used when separating water and concentrating an acetic acid stream. The former is often performed under negative pressure while the latter is often performed under ambient pressure, though this is not exclusive or required. Parameters will depend on the flow rate of the feed streams, amount of water contained in the hydrolyzed product stream, amount of acid in the acetyl feed composition during anhydride mode, and level of purity desired in the resulting concentrated streams. In addition, the column should contain sufficient stages and capacity. In some embodiments, the separation column has a diameter (in feet) equal to at least about the product of about 0.35 multiplied by the square root of the maximum rate (in gallons per minute) at which compositions are to be fed to the column. In some embodiments, the "0.35" in the foregoing sentence is replaced by 0.30, 0.40, 0.50, 0.69, 0.70, 0.80, 1.00, 1.25, 1.50, 1.75, 2.00 or 2.25.

In some embodiments of the anhydride mode, the separation zone or process is a distillation column operated at a head pressure of from about 10 to about 1500 torr. In some embodiments, the head pressure is from about 50 to about 400 torr. In some embodiments, the head pressure is from about 100 to about 200 torr. While any distillate composition is within the scope of the invention, higher concentrations of acid and lower concentrations of anhydride are the result of better separation. In some embodiments, the head temperature of the column is such that the distillate anhydride weight composition is from about 0.5% to about 50%. Anhydride mode embodiments also exist in which the head temperature of the column is such that the distillate anhydride weight composition is, for example, from about 0.5% to about 25%, from about 1% to about 25%, from about 5% to about 25%, from about 8% to about 15%, or from about 5% to about 15%. In some embodiments, the column is operated with a reflux ratio of from about 1 to about 20. Embodiments also exist in which the column is operated with a reflux ratio of, for example, from about from about 2 to about 6 or from about 2.5 to about 3.

In the acid mode, pressure is a more flexible parameter and the distillation column is operated at any suitable or desired pressure. In some embodiments, the column is operated at ambient pressure. In some embodiments, the column is operated at a pressure of from about 700 to about 800 torr in acid mode. In some embodiments, the head temperature of the column is such that the distillate acetic acid weight composition is from about 1% to about 99%. In some embodiments, the head temperature of the column is such that the distillate acetic acid weight composition is, for example, from about 20% to about 90%, from about 5% to about 30%, from about 10% to about 20%, from about 20% to about 50% or from about 70% to about 80%. The column is operated with a reflux ratio of from about 2 to about 20. In some embodiments, the column is operated with a reflux ratio of, for example, from about 7 to about 15, from about 8 to about 12 or from about 9 to about 11. In some embodiments, an azeotroping agent may be added to facilitate separation of water from the acetic acid stream by forming an azeotrope with water having a boiling point that is lower than the normal boiling point of water. Any effective azeotroping agent may be used.

In the anhydride mode, at least about 50% of the acetyl feed composition bypasses the hydrolysis process and is fed to the first separation zone or process to separate at least some of the acetic acid from the acetic anhydride in the liquid feed composition. In various embodiments, the amount of the acetyl feed composition that bypasses the hydrolysis process in anhydride mode is at least about 60%, at least about 70%, at least about 80%, at least about 90%, at least about 95%, at least about 97.5%, at least about 99% or at least about 99.5%. The hydrolysis process can be bypassed in any suitable way. For example, embodiments exist in which acetyl feed compositions (or portions thereof) bypass the hydrolysis process by bypassing the hydrolysis zone entirely, by being fed to the hydrolysis zone without being hydrolyzed there, or both. Hydrolysis can be reduced or stopped in the hydrolysis zone in any manner, but in some embodiments, feed of water to the hydrolysis zone is reduced or eliminated. The separation process in anhydride mode results in a concentrated stream containing concentrated acetic anhydride having a desired level of purity as well as a separated stream containing anhydride and acid.

In the acid mode, more than about 50% of the acetyl feed composition undergoes the hydrolysis process before it is fed to the first separation zone or process to separate at least some of the water from the acetic acid in the stream fed to the first separation zone or process. In various embodiments, the amount of the acetyl feed composition that undergoes hydrolysis process in acid mode is at least about 60%, at least about 70%, at least about 80%, at least about 90%, at least about 95%, at least about 97.5%, at least about 99% or at least about 99.5%.

The separated stream in anhydride mode will contain relative amounts of acetic acid and acetic anhydride that depend on the above parameters, and the amount of acetic acid in the composition that is fed to the separation zone or process. In some embodiments of the anhydride mode, the anhydride concentrated stream contains at least 80% anhydride. Embodiments also exist in which the anhydride concentrated stream contains at least 85%, at least 90%, at least 95%, at least 97%, at least 98%, at least 99%, at least 99.5%, at least 99.75%, or at least 99.8% anhydride. In some embodiments of anhydride mode, the separated stream contains from about 0.5 to about 99.5% acid.

In acid mode, the separated stream will contain relative amounts of water and acetic acid that depend on the above parameters, and the amount of water in the hydrolyzed product stream that is fed to the separation zone or process. In some embodiments of acid mode, the separated stream contains between 0.5 and 95% water. In some embodiments of acid mode, the separated stream contains between 0.5 and 50% water. In some embodiments of acid mode, the separated stream contains between 0.5 and 25% water. In some embodiments of acid mode, the separated stream contains between 0.5 and 10% water. In some embodiments of acid mode, the separated stream contains between 10 and 20% water. In some embodiments of acid mode, the separated stream contains between 25 and 50% water. In some embodiments of acid mode, the separated stream contains between 25 and 40% water. In some embodiments of acid mode, the separated stream contains between 40 and 55% water. In some embodiments of acid mode, the amount of water in the separated stream may increase over time, as increasing stoichiometric excess of water fed to the hydrolysis zone may compensate for added hydrolysis catalyst becoming spent or otherwise experiencing diminished efficacy with age or continued use.

Conveyance Components

The systems of the invention further include conveyance components for transporting materials into, throughout and out of the system. All type and function of conveyance components are within the invention. Conveyance components include, for example, one or more feed conveyance components configured to allow transportation of acetyl feed compositions into either the first separation zone or process, the hydrolysis zone, or both. Another example is hydrolyzed product conveyance components, which can be configured to transport at least some of the hydrolyzed product streams to separation zones and processes of the invention.

The conveyance components thus include components providing the ability to feed acetyl feed compositions to the hydrolysis zone or process prior to feeding them to the separation zone or process, bypassing the hydrolysis zone or process and proceeding to the separation zone or process, or both.

Any type of suitable conveyance components can be used. Some examples include piping and ductwork, pumps, valves, storage equipment such as tanks, heat exchangers, related instrumentation and control systems and the like.

Conveyance of a composition, stream or material from one particular zone, vessel or process to another is not limited to to direct conveyance, in which the material travels through the conveyance without contacting other zones, vessels or processes. Both direct conveyance and indirect conveyance (in which a composition, stream or material travels through or contacts other zones, vessels or processes before reaching its destination) are within the meaning of the term "conveyance."

Further Processing and Use of Streams

In some embodiments, the concentrated stream from the first separation zone or process may be processed further. For example, the purity of the concentrated stream may be improved by further separation processes, such as membrane processes, ion exchange, filtration or distillation to remove impurities such as high-boiling compounds such as color bodies or corrosion metals. Any type of desired or useful additional processing may be used with the invention.

In some embodiments, at least one second separation process or zone is used in anhydride mode to concentrate acetic anhydride in a concentrated stream and is used in acid mode to concentrate acetic acid in a concentrated stream. Such second separation zones or processes are useful to concentrate impurities in acid or anhydride product into one or more second separated streams. The second separation process or zone is capable of operating in a second anhydride mode and a second acid mode, and therefore is capable of changing back and forth between the second anhydride mode and the second acid mode. In some embodiments, the impurities concentrated into one or more second separated streams are higher boiling impurities, lower boiler impurities, or both. In referring to a particular product stream, "higher boiling impurities" refers to the impurities that have a boiling point higher than that of the product and "lower boiling impurities" refers to the impurities that have a boiling point lower than that of the product acid or anhydride in which they are present. Thus, in an acetic anhydride stream, "higher boiling impurities" refers to the impurities that have a boiling point higher, and "lower boiling impurities" refers to the impurities that have a boiling point lower, than that of the acetic anhydride present in the product stream. "Boiling points" of particular components refer to the components as they exist in stream, taking into account ambient conditions, the existence of azeotroping components, and other factors.

Some examples of higher boiling impurities that may be concentrated into separated streams in various embodiments include corrosion metals, (such as iron, nickel, chromium, and the like), catalyst resides from upstream processes, (such as catalyst metals or salts thereof, catalyst resins, and residues from hydrolysis catalysts such as p-toluenesulfonic acid, certain iodine containing compounds), tars resulting from decomposition of process material (especially in acetic anhydride mode), carboxylic acids or anhydrides other than acetic acid or acetic anhydride, ethylidene diacetate, solids and color causing impurities. Some examples of lower boiling impurities that may be concentrated into separated streams in various embodiments include methyl acetate, acetaldehyde, methanol, water, acetone and methyl iodide. Embodiments exist with various combinations of two or more of the low-boiling and high-boiling impurities listed above.

In some embodiments, the second separation zone or process includes a distillation system including a vessel or column) that concentrates product (anhydride in anhydride mode; acid in acid mode) in a second concentrated stream and concentrates impurities in at least one second separated stream. In some embodiments, the second concentrated stream is taken from the distillation vessel at a location that is vertically above a location at which at least one second separated stream containing concentrated higher boiling impurities is removed. In some embodiments, the second concentrated stream is taken from the vessel at a location that is vertically below a location at which a second separated stream containing concentrated lower boiling impurities is removed. Any effective configuration is within the invention. For example, embodiments also exist in which the second concentrated stream is removed as a column overhead or first sidedraw a second separated stream is removed either as a column underflow or vertically lower second sidedraw. In some such embodiments, the second concentrated stream is removed as a column overhead and the second separated stream is removed as a column underflow. Similarly, embodiments exist in which the second concentrated stream is removed as a column underflow or first sidedraw and a second separated stream is removed either as a column overhead or vertically higher second sidedraw. In some such embodiments, the second concentrated stream is removed as a column underflow and the second separated stream is removed as a column sidedraw. In some embodiments separated streams are removed from the distillation vessel at two or more locations, wherein: (a) at least one of the locations is vertically above a location at which the second concentrated stream is removed and removes a separated stream containing lower boiling impurities; and (b) at least one other of the locations is vertically below the location at which the second concentrated stream is removed, and removes a separated stream containing concentrated higher boiling impurities. An example of such an embodiment is a distillation configuration in which the second concentrated stream is removed as a first sidedraw while a second separated stream containing concentrated higher boiling impurities is removed as an underflow or a second sidedraw that is vertically lower than the first sidedraw and a third separated stream containing concentrated lower boiling impurities is removed as an overhead or a third side draw that is vertically higher than the first sidedraw.

As with the first separation zone and process, the equipment and parameters of any additional separation zone or process used to conduct separation in both anhydride mode and acid mode are not critical as any effective equipment or process for separating the streams in each mode may be used. The equipment is sized and constructed in a manner that will accommodate the difference in parameters between acid mode and anhydride mode. In some embodiments, the separation process is a column having a diameter (in feet) equal to at least the product of about 0.22 multiplied by the square root of the maximum rate (in gallons per minute) at which compositions are to be fed to the column. In some embodiments, the "0.22" in the foregoing sentence is replaced by 0.35, 0.45, 0.60, 0.80, 0.90, 1.00, 1.20, 1.40. or 1.50.

In some embodiments, a second distillation column is used. In some embodiments of the anhydride mode, the second column is operated at a head pressure of from about 10 to about 1500 torr. In some embodiments, the head pressure in anhydride mode is from about 50 to about 400 torr. In some embodiments, the head pressure in anhydride mode is from about 100 to about 200 torr. In some embodiments, the distillate acetic acid composition by weight composition is from about 0.05% to about 0.5%. In some embodiments, the distillate acetic acid composition by weight composition is from about 0.1% to about 0.3%. In some embodiments, the second column is operated with a reflux ratio of from about 0.1 to about 3.0. In some embodiments, the second column is operated with a reflux ratio of from about 0.2 to about 1.0. In some embodiments, the second column is operated with a reflux ratio of from about 0.2 to about 0.3.

In the acid mode, pressure is a more flexible parameter and the distillation column is operated at any suitable or desired pressure. In some embodiments, the column is operation at ambient pressure. In some embodiments, the column is operated at a pressure of from about 700 to about 800 torr in acid mode. In some embodiments of acid mode, the second column is operated with a reflux ratio from about 0.1 to about 3. In some embodiments of acid mode, the second column is operated with a reflux ratio from about 0.2 to about 1.0. In some embodiments of acid mode, the second column is operated with a reflux ratio from about 0.2 to about 0.3.

The second separation zone or process is an optional feature found in some embodiments, and the invention is not limited to embodiments having a second separation zone or process. Similarly, more than two separation zones or processes are used in some embodiments. Any number of additional separation zones or processes may be used where suitable to remove additional higher-boiling or lower-boiling impurities.

Uses of Byproduct Streams

The separated streams from the separation zones or processes may be disposed of or used in any useful manner. For example, water and acid streams may be used in any process where a dilute stream of acetic acid in water is useful. Some examples include use of dilute streams of acetic acid in water in processes for production of methyl acetate from methanol and acetic acid or in processes for production of acetic acid through hydrolysis of acetic anhydride.

In some embodiments, a separated water and acid stream from the separation zone or process is recycled to the hydrolysis zone or process of the process. Where the separated stream is a heated stream such as a distillation overhead or sidedraw, it can be chilled and condensed before recycling. Any standard method or equipment for condensation or chilling may be used. The stream may be recycled to the hydrolysis zone by introducing it directly to the hydrolysis zone or combining it with one or more feeds to the hydrolysis zone.

In some embodiments involving a recycle stream, the water levels in the recycle stream are measured, for example by using an in-stream monitor. Several such monitors and other methods and devices for measurement are commercially available, and any effective monitoring device suitable for the stream may be used. The monitor may measure the recycle stream itself or a feed line that includes the recycle stream combined with other feed components. This monitor can provide a feedback loop to indicate variation in the stoichiometric excess of water in the feed to the hydrolysis zone. As such, the feedback from the monitor may be used as a basis for controlling or adjusting the rate of fresh water added to the hydrolysis zone or process. This may be accomplished manually or through an automated control loop. In some embodiments, a decision is made about whether or not to adjust the feed rate of stoichiometric excess of water to the hydrolysis process based on the measurement of the water content in the separated stream and, if the decision is to adjust the flow rate, an adjustment of the flow rate is made in accordance with the decision. In some embodiments, the decision to adjust feed rate includes a decision as to the extent to which water feed rate needs to be adjusted, and the amount of adjustment is in accordance with the decision.

Separated overhead or sidedraw streams containing small amounts of acetic anhydride in acid may be used for any acceptable purpose. In some embodiments, such streams are fed to processes used to manufacture esters from mixed acid/ anhydride, such as the methyl acetate process described in U.S. Pat. No. 4,939,294.

Thus, the processes of the present invention may include any of the foregoing further processing steps. Similarly, the systems of the present invention may include first separated stream recycling components to recycle separated streams to other locations in the process. One example of such other locations is the hydrolysis zone. Thus, in some embodiments, at least some of the first separated stream is recycled to the hydrolysis zone or process. The systems of the present invention may include first separated stream recycling components to transfer separated streams to other processes, systems or equipment for use.

The various aspects of the present invention can be further illustrated and described by the following Examples. It should be understood, however, that these Examples are included merely for purposes of illustration and are not intended to limit the scope of the invention, unless otherwise specifically indicated.

EXAMPLE

A process for preparing concentrated acetic acid and acetic anhydride streams from liquid acetyls streams fed at a rate of 500 parts per hour is configured to allow feed streams to be fed to a hydrolysis zone or to a first distillation column. The distillation column is constructed of 316 L stainless steel having 20 ideal stages. The feed point is at the 8th ideal stage from the top. The column is capable of being operated at either ambient or negative pressure and has a diameter (in feet) equal to at least the product of 0.34 multiplied by the square root of the maximum rate (in gallons per minute) at which compositions are to be fed to the column.

The hydrolysis zone is a simple reactor composed of Hastalloy C-276 and having a volume of 1600 volumetric parts (i.e. parts having the same volume as the volumetric component of the parts per hour feed). A heat exchanger for non-contact cooling (with water) of feeds to the vessel is available for this equipment, but is not used in this particular run. The vessel is a single bed packed with AMBERLYST 15, a styrene divinylbenzene copolymer functionalized with sulfonic acid groups and available from Rohm & Haas, Philadelphia, Pa. The bed is sized and charged to provide a superficial residence time of at least 10 minutes for the stream. The hydrolysis zone is configured to feed its underflow to the first column.

In acid mode, a continuous stream containing 95% acetic acid and 5% acetic anhydride by weight and a temperature of from about 40 to about 45° C. is fed at a flow rate of 500 parts per hour in addition to a recycle stream (described below) from the overhead from the first column of 48 parts per hour of 75% acetic acid and 25% water to the hydrolysis zone. Parts per hour as described in this example are mass. The stream is combined with a demineralized water steam flowing at a rate of 84 parts per hour while being fed.

The underflow from the hydrolysis zone is fed at a rate of 632 parts per hour to a distillation column operated with a reflux ratio of about 10.1, a head pressure of about 760 torr and head temperature such that the distillate acid weight composition is 75 wt %. The underflow of the distillation column contains at least 99.8% acetic acid, and the overhead of the distillation column contains about 75% acetic acid to about 25% water. The overhead from the column is condensed to a temperature of 62° C. and is piped at a rate of 48 parts per hour to combine with the original feed stream containing acetic acid and acetic anhydride and the water stream, (as described above), so that the three streams are fed together to the hydrolysis zone.

The underflow is fed at a rate of 584 parts per hour to the second column, with a reflux ratio of about 0.25 and a head pressure of about 760 torr. The final acetic acid product from the second distillation column is produced as an overhead at a rate of 555 parts per hour and, as compared to the feed underflow from the first column, has reduced level of impurities having boiling points higher than acetic acid.

In anhydride mode, a continuous stream containing 30% acetic acid and 70% acetic anhydride by weight and a temperature from about 20 to about 150 C is fed at a flow rate of 500 parts per hour directly to the first distillation column. The distillation column is operated with a reflux ratio of about 2.7, a head pressure of about 150 torr and a head temperature such that the distillate anhydride composition is 10 wt %. The underflow of the distillation column contains about 99.5% acetic anhydride, and the overhead of the distillation column contains about 90% acetic acid and about 10% acetic anhydride. The underflow is fed at a rate of 335 parts per hour to the second column, with a reflux ratio of about 0.25 and a head pressure of about 150 torr. The final acetic anhydride product from the second distillation column is condensed and has reduced levels of high boiling contaminants as compared to the feed.

In either mode, the overhead from the distillation column condensed and used or recycled in any of a variety of ways. The underflow from the distillation column is fed to a second distillation column to separate corrosion metals and low boiling impurities from the product. This second column has 6 trays and a diameter (in feet) equal to at least the product of 0.34 multiplied by the square root of the maximum rate (in gallons per minute) at which compositions are to be fed to the column. The material enters the column beneath the bottom tray. The overhead stream from the second column is the concentrated product.

The inventors hereby state their intent to rely on the Doctrine of Equivalents to determine and assess the reasonably fair scope of the present invention as pertains to any apparatus not materially departing from but outside the literal scope of the invention as set forth in the following claims.

What is claimed is:

1. A system for processing at least one acetyl feed composition, such acetyl feed composition comprising acetic acid and acetic anhydride, wherein the system comprises:
   a first separation zone configured in a manner to separate a first separated stream from a first concentrated stream, and further configured such that the separation zone can be operated in an acid mode and can be operated in an anhydride mode;
   at least one hydrolysis zone capable of operating a hydrolysis process to hydrolyze at least some acetic anhydride in the at least one acetyl feed composition to result in a hydrolyzed product stream comprising acetic acid and water;
   at least one feed conveyance component configured to allow transportation of at least some of the at least one acetyl feed composition to the first separation zone, the hydrolysis zone, or both; and
   at least one hydrolyzed product conveyance component configured to allow transportation of at least some of the hydrolyzed product stream to the at least one first separation zone,
   wherein:
   the acid mode comprises processing at least some of the hydrolyzed product stream in the first separation zone such that the first separated stream comprises water and the first concentrated stream comprises concentrated acetic acid, and
   the anhydride mode comprises processing at least some of the acetyl feed composition in the first separation zone such that the first separated stream comprises acetic acid and the first concentrated stream comprises concentrated acetic anhydride,
   and wherein the at least one feed conveyance component and the hydrolysis process are configured such that:
   (a) while the first separation zone operates in the acid mode, the hydrolysis process can be operated in the hydrolysis zone and more than about 50% by weight of the acetyl feed composition can be fed to the hydrolysis zone; and
   (b) while the first separation zone operates in the anhydride mode at least about 50% by weight of the acetyl feed composition can be fed to the separation zone without undergoing a hydrolysis process.

2. The system of claim 1, wherein while the first separation zone operates in the anhydride mode, at least about 50% of the acetyl feed composition can travel through the hydrolysis zone without undergoing a hydrolysis process before being fed to the first separation zone.

3. The system of claim 1, wherein while the first separation zone operates in the anhydride mode, at least about 50% of the acetyl feed composition can be fed to fed to the first separation zone without first being fed to the hydrolysis zone.

4. The system of claim 1, wherein the system further comprises at least one first separated stream recycling component capable of recycling at least some of the first separated stream to the hydrolysis zone.

5. The system of claim 1, wherein the system further comprises at least one first separated stream transfer component capable of transferring at least some of the first separated stream to at least one additional equipment or process.

6. The system of claim 5, wherein the at least one additional equipment or process comprises an esterification process.

7. The system of claim 1, wherein the system further comprises cooling components capable of removing heat from at least part of the hydrolysis zone, at least some of the feed to the hydrolysis zone, or both.

8. The system of claim 1, wherein the first separation zone comprises a distillation column, the first separated stream is removed from at least one first location on the distillation column, the first concentrated stream is removed from at least one second location on the distillation column and the first location is vertically above the second location.

9. The system of claim 8, wherein the first separated stream comprises at least one distillation overhead or first sidedraw from the distillation column and the first concentrated stream comprises at least one distillation underflow or second sidedraw from the distillation column.

10. The system of claim 8, wherein the first separated stream comprises at least one distillation overhead from the distillation column and the first concentrated stream comprises at least one distillation underflow from the distillation column.

11. The system of claim 8, wherein the first separated stream comprises at least one distillation overhead from the distillation column, the first concentrated stream comprises at least one sidedraw from the distillation column, and the system is capable of removing an underflow separated stream as a distillation underflow from the distillation column.

12. The system of claim 1, further comprising at least one second separation zone configured to receive at least some of the first concentrated stream from the first separation zone and to separate at least one second separated stream from a second concentrated stream, and further configured to operate in either a second separation zone acid mode or a second separation zone anhydride mode, wherein:

the second separation zone acid mode comprises processing at least some of the first concentrated stream in the second separation zone such that the at least one second separated stream comprises concentrated impurities and the second concentrated stream comprises concentrated acetic acid, and the second separation zone anhydride mode comprises processing at least some of the first concentrated stream in the second separation zone such that the at least one second separated stream comprises concentrated impurities and the second concentrated stream comprises concentrated acetic anhydride.

13. The system of claim 12, wherein the second separation zone comprises a second distillation column, the at least one second separated stream is removed from at least one first location on the second distillation column, the second concentrated stream is removed from at least one second location on the second distillation column and the at least one first location is vertically below the second location.

14. The system of claim 12, wherein the at least one second separated stream comprises at least one distillation underflow or second sidedraw from the second distillation column and the second concentrated stream comprises at least one distillation overhead or first sidedraw from the second distillation column.

15. The system of claim 12, wherein the at least one second separated stream comprises at least one distillation underflow from the second distillation column and the second concentrated stream comprises at least one distillation overhead from the second distillation column.

16. The system of claim 12, wherein the at least one second separated stream comprises at least one distillation underflow from the second distillation column, the second concentrated stream comprises at least one sidedraw from the second distillation column, and a third separated stream is removed as a distillation overhead from the second distillation column.

17. The system of claim 1, wherein the system further comprises at least one upstream production system capable of producing the acetyl feed composition, wherein the at least one upstream production system is configured to allow:

operation in an upstream process acid mode to produce an acid mode acetyl feed composition; and operation in an upstream process anhydride mode to produce an anhydride mode acetyl feed composition, wherein the acid mode acetyl feed composition has an acid:anhydride ratio having an acid number that is at least about 10 higher than an acid number of the anhydride mode acetyl feed composition.

18. The system of claim 17, wherein the acid mode acetyl feed composition has an acid:anhydride ratio having an acid number that is at least about 50 higher than an acid number of the anhydride mode acetyl feed composition.

19. The system of claim 17, wherein the at least one upstream production system is configured to allow combining at least part of the at least one acetyl feed composition with at least some water, at least some methanol or both.

20. The system of claim 17, wherein the at least one upstream production system comprises at least one carbonylation system capable of reacting carbonylation process feed compounds to produce a carbonylation product comprising acetic acid, acetic anhydride or a combination thereof.

21. The system of claim 20, wherein the system is configured to allow varying the weight ratio of methanol to total anhydride-forming reactants that form acetic anhydride in the carbonylation process feed compounds, wherein total anhydride-forming is the sum of amounts of methyl acetate and dimethyl ether in the carbonylation process feed compounds.

22. The system of claim 20, wherein the at least one upstream production system is configured to allow combining at least some of the carbonylation product with at least some water, at least some methanol or both.

23. A process comprising:
for a first period of time, operating the system of claim 1 in acid mode; and
for a second period of time that is not concurrent with the first period of time, operating the system claim 1 in anhydride mode.

24. The process of claim 23 wherein the at least one acetyl feed composition during the first period of time has an acid number in the acid:anhydride ratio that is no more than about 10 higher than the acid number in the acid:anhydride ratio of the at least one acetyl feed composition as the feed during the second period of time.

25. The process of claim 23 wherein the at least one acetyl feed composition during the first period of time has an acid number in the acid:anhydride ratio that is at least about 20 higher than the acid number in the acid:anhydride ratio of the at least one acetyl feed composition as the feed during the second period of time.

26. A process for processing a plurality of acetyl feed compositions comprising acetic acid and acetic anhydride, comprising:

a) operating a first separation process configured in a manner to separate compositions into a first separated stream and a first concentrated stream, and further configured to operate in either an acid mode or an anhydride mode;

b) while operating the first separation process in an acid mode, hydrolyzing at least one first acetyl feed composition in a hydrolysis process in a hydrolysis zone to produce a hydrolyzed product stream comprising acetic acid and water, and feeding at least some of the hydrolyzed product stream to the first separation process; and c) while operating the first separation process in an anhydride mode, bypassing at least one second acetyl feed composition around the hydrolysis process and feeding it to the first separation process, wherein:

the acid mode comprises operating the first separation process such that the first separated stream comprises water and the first concentrated stream comprises concentrated acetic acid, and the anhydride mode comprises operating the first separation process such that the first separated stream comprises acetic acid and the first concentrated stream comprises concentrated acetic anhydride.

27. The process of claim 26 wherein the at least one first acetyl feed composition has an acid number in the acid:anhydride ratio that is no more than about 10 higher than the acid number in the acid:anhydride ratio of the second acetyl feed composition.

28. The process of claim 26 wherein the at least one first acetyl feed composition has an acid number in the acid:anhydride ratio that is at least about 20 higher than the acid number in the acid:anhydride ratio of the second acetyl feed composition.

29. The process of claim 26, wherein bypassing at least one second acetyl feed composition around the hydrolysis process comprises passing at least some of the at least one second acetyl feed composition through the hydrolysis zone without undergoing a hydrolysis process before being fed to the first separation zone.

30. The process of claim 26, wherein bypassing at least one second acetyl feed composition around the hydrolysis process and feeding at least some of the at least one second acetyl feed composition to the first separation zone without first feeding it the hydrolysis zone.

31. The process of claim 26, wherein the process further comprises recycling at least some of the first separated stream to the hydrolysis zone while the first separation process is operating in acid mode.

32. The process of claim 26, wherein the process further comprises transferring at least some of the first separated stream to at least one additional equipment or process.

33. The process of claim 32, wherein the at least one additional equipment or process comprises an esterification process.

34. The process of claim 26, wherein the process further comprises cooling at least part of the hydrolysis zone, at least some of the feed to the hydrolysis zone, or both.

35. The process of claim 26, wherein the first separation zone comprises a distillation column, the first separated stream is removed from at least one first location on the distillation column, the first concentrated stream is removed from at least one second location on the distillation column, and the first location is vertically below the second location.

36. The process of claim 35, wherein the first separated stream comprises at least one distillation overhead or first sidedraw from the distillation column and the first concentrated stream comprises at least one distillation underflow or second sidedraw from the distillation column.

37. The process of claim 35, wherein the first separated stream comprises at least one distillation overhead from the distillation column and the first concentrated stream comprises at least one distillation underflow from the distillation column.

38. The process of claim 35, wherein the first separated stream comprises at least one distillation overhead from the distillation column, the first concentrated stream comprises at least one sidedraw from the distillation column, and an underflow separated stream is removed as a distillation underflow from the distillation column.

39. The process of claim 26, further comprising feeding at least some of the first concentrated stream to at least one second separation zone and withdrawing from the second separation zone a second separated stream from a second concentrated stream, wherein:
the at least one second separation zone is configured to operate in either a second separation zone acid mode or a second separation zone anhydride mode;
the at least one second separation zone acid mode comprises processing at least some of the first concentrated stream in the at least one second separation zone such that the second separated stream comprises concentrated impurities and the second concentrated stream comprises concentrated acetic acid, and
the at least one second separation zone anhydride mode comprises processing at least some of the first concentrated stream in the second separation zone such that the second separated stream comprises concentrated impurities and the second concentrated stream comprises concentrated acetic anhydride.

40. The process of claim 39, further comprising:
operating the at least one second separation zone in second separation zone acid mode while operating the at least one first separation zone in acid mode, and
operating the at least one second separation zone in anhydride mode while operating the at least one first separation zone in anhydride mode.

41. The process of claim 39, wherein the second separation zone comprises a second distillation column, the at least one second separated stream is removed from at least one first location on the second distillation column, the second concentrated stream is removed from at least one second location on the second distillation column and the first location is vertically below the second location.

42. The process of claim 41, wherein the at least one second separated stream comprises at least one distillation underflow or second sidedraw from the second distillation column and the second concentrated stream comprises at least one distillation overhead or sidedraw from the second distillation column.

43. The process of claim 41, wherein the at least one second separated stream comprises at least one distillation underflow from the second distillation column and the second concentrated stream comprises at least one distillation overhead from the second distillation column.

44. The process of claim 41, wherein the at least one second separated stream comprises at least one distillation underflow from the second distillation column, the second concentrated stream comprises at least one sidedraw from the second distillation column, and a third separated stream is removed as a distillation overhead from the second distillation column.

45. The process of claim 26, wherein the process further comprises:
operating at least one upstream process in an upstream process acid mode to produce an acid mode acetyl feed composition; and
operating the at least one upstream process in an upstream process anhydride mode to produce an anhydride mode acetyl feed composition,
wherein:
the acid mode acetyl feed composition has an acid:anhydride ratio having an acid number that is at least about 10 higher than an acid number of the anhydride mode acetyl feed composition;
at least one first acetyl feed composition is an acid mode acetyl feed composition; and
at least one second acetyl feed composition is an anhydride mode acetyl feed composition.

46. The process of claim 45, wherein the acid mode acetyl feed composition has an acid:anhydride ratio having an acid number that is at least about 50 higher than an acid number of the anhydride mode acetyl feed composition.

47. The process of claim 45, wherein the upstream process acid mode comprises combining at least one acetyl feed composition with at least some water, at least some methanol or both.

48. The process of any claim 45, wherein the at least one upstream process comprises at least one carbonylation process comprising reacting carbonylation process feed compounds to produce a carbonylation product comprising acetic acid and acetic anhydride.

49. The process of claim 48, wherein:
the carbonylation process comprises carbonylating methanol and at least one anhydride-forming reactant, wherein the at least one anhydride-forming reactant is selected from acetic anhydride, dimethyl ether, or a combination thereof;
upstream process acid mode comprises feeding the carbonylation process in a weight ratio of methanol to total reactants that form acetic anhydride that is higher than the weight ratio of methanol to total reactants that form acetic anhydride in upstream process anhydride mode; and total reactants that form acetic anhydride is the sum of amounts of acetic anhydride and dimethyl ether in the carbonylation process feed compounds.

* * * * *